(12) United States Patent
Fichtl (10) Patent No.: US 9,567,264 B2
(45) Date of Patent: Feb. 14, 2017

(54) PROCESS FOR PRODUCING DIESEL FUEL AND AVIATION FUEL FROM RENEWABLE FEEDSTOCKS HAVING IMPROVING YIELDS

(71) Applicant: UOP LLC, Des Plaines, IL (US)

(72) Inventor: Geoffrey W. Fichtl, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 146 days.

(21) Appl. No.: 14/675,223

(22) Filed: Mar. 31, 2015

(65) Prior Publication Data

US 2016/0289135 A1 Oct. 6, 2016

(51) Int. Cl.
| | | |
|---|---|---|
| C07C 1/20 | (2006.01) | |
| C07C 4/06 | (2006.01) | |
| C07C 1/207 | (2006.01) | |
| C07C 5/27 | (2006.01) | |
| C10L 1/08 | (2006.01) | |
| C10L 1/04 | (2006.01) | |

(52) U.S. Cl.
CPC ............... *C07C 1/20* (2013.01); *C07C 1/2076* (2013.01); *C07C 1/2078* (2013.01); *C07C 4/06* (2013.01); *C07C 5/277* (2013.01); *C10L 1/04* (2013.01); *C10L 1/08* (2013.01); *C10L 2270/026* (2013.01); *C10L 2270/04* (2013.01); *C10L 2290/543* (2013.01)

(58) Field of Classification Search
None
See application file for complete search history.

(56) References Cited

U.S. PATENT DOCUMENTS

| | | |
|---|---|---|
| 7,888,542 B2 | 2/2011 | Koivusalmi et al. |
| 7,999,142 B2 | 8/2011 | Kalnes et al. |
| 8,039,682 B2 | 10/2011 | McCall et al. |
| 8,193,399 B2 | 6/2012 | Gosling |
| 8,198,492 B2 | 6/2012 | Brady et al. |
| 8,304,592 B2 | 11/2012 | Luebke |

(Continued)

FOREIGN PATENT DOCUMENTS

WO   WO 2011/011588 A1   1/2011

OTHER PUBLICATIONS

Chen et al., "Impact of composition and molecular structure upon the cold flow properties . . . ," Acta Petrolei Sinica (Petroleum Processing Section) (2009), 25(5), 673-677.

(Continued)

*Primary Examiner* — Tam M Nguyen (57) ABSTRACT

A process for producing aviation fuel and diesel from renewable feedstock is described. This process involves introducing the renewable feedstock into a hydrogenation and deoxygenation zone, and separating the hydrocarbon effluent from the hydrogenation and deoxygenation zone into an aviation boiling range fraction and a diesel boiling range fraction. The aviation boiling range fraction and diesel boiling range fraction are alternately sent to the isomerization and selective hydrocracking zone. This allows for lower severity isomerization and selective hydrocracking zone operating conditions when processing oils that naturally contain medium and long carbon chains ($C_8$-$C_{18}$), such as coconut or palm kernel oil. The lower severity operation results in decreased cracking, increasing the yield of aviation fuel product.

20 Claims, 2 Drawing Sheets

(56) References Cited

U.S. PATENT DOCUMENTS

| | | |
|---|---|---|
| 8,314,274 B2 | 11/2012 | Marker et al. |
| 8,471,079 B2 | 6/2013 | Brandvold et al. |
| 8,507,741 B2 | 8/2013 | Anumakonda et al. |
| 8,546,629 B2 | 10/2013 | Bozzano et al. |
| 8,753,853 B2 | 6/2014 | Ritter et al. |
| 8,916,739 B2 | 12/2014 | Fichtl et al. |
| 2011/0203253 A1 | 8/2011 | Derr et al. |
| 2012/0283491 A1 | 11/2012 | Zhou et al. |
| 2014/0005450 A1 | 1/2014 | Marker et al. |
| 2014/0296590 A1* | 10/2014 | Luebke ............ C10G 3/52 585/310 |
| 2015/0094506 A1* | 4/2015 | Fichtl ............ C10G 3/50 585/310 |

OTHER PUBLICATIONS

Serrano et al., "Influence and blending vegetable oil methyl esters on biodiesel fuel properties: Oxidative and cold flow properties", Energy (2014), v. 65, 109-115.

Bejan et al., "Effect of different alcohols and palm and palm kernel (palmist) oils on biofuel properties for special uses", Energy & Fuels (2014), 28(8), 5128-5135.

* cited by examiner

PROCESS FOR PRODUCING DIESEL FUEL AND AVIATION FUEL FROM RENEWABLE FEEDSTOCKS HAVING IMPROVING YIELDS

BACKGROUND OF THE INVENTION

As the demand for diesel fuel and aviation fuel increases worldwide, there is increasing interest in sources other than petroleum crude oil for producing the fuels. One such source is what has been termed renewable sources. These renewable sources include, but are not limited to, plant oils such as corn, rapeseed, canola, soybean and algal oils, animal fats such as inedible tallow, fish oils, and various waste streams such as yellow and brown greases and sewage sludge. The common feature of these sources is that they are composed of glycerides and Free Fatty Acids (FFA). Both of these compounds contain aliphatic carbon chains having from about 8 to about 24 carbon atoms. The aliphatic carbon chains in the glycerides or FFAs can be saturated or mono-, di- or poly-unsaturated. The glycerides may be tri-glycerides, di-glycerides, mono-glycerides, or any combination thereof.

There are reports in the art disclosing the production of hydrocarbons from oils. For example, U.S. Pat. No. 4,300,009 discloses the use of crystalline aluminosilicate zeolites to convert plant oils such as corn oil to hydrocarbons such as gasoline and chemicals such as para-xylene. U.S. Pat. No. 4,992,605 discloses the production of hydrocarbon products in the diesel boiling range by hydroprocessing vegetable oils such as canola or sunflower oil. Finally, US Publication No. 2004/0230085 discloses a process for treating a hydrocarbon component of biological origin by hydrodeoxygenation followed by isomerization.

Processes for producing two fuels, such as a diesel fuel and an aviation fuel, from renewable feedstocks are also known. The aviation fuel is produced via operation of the isomerization/cracking reactor in a higher severity mode to induce greater isomerization and cracking on longer chain n-paraffins (typically $nC_{15}$-$nC_{18}$).

Figure 1:
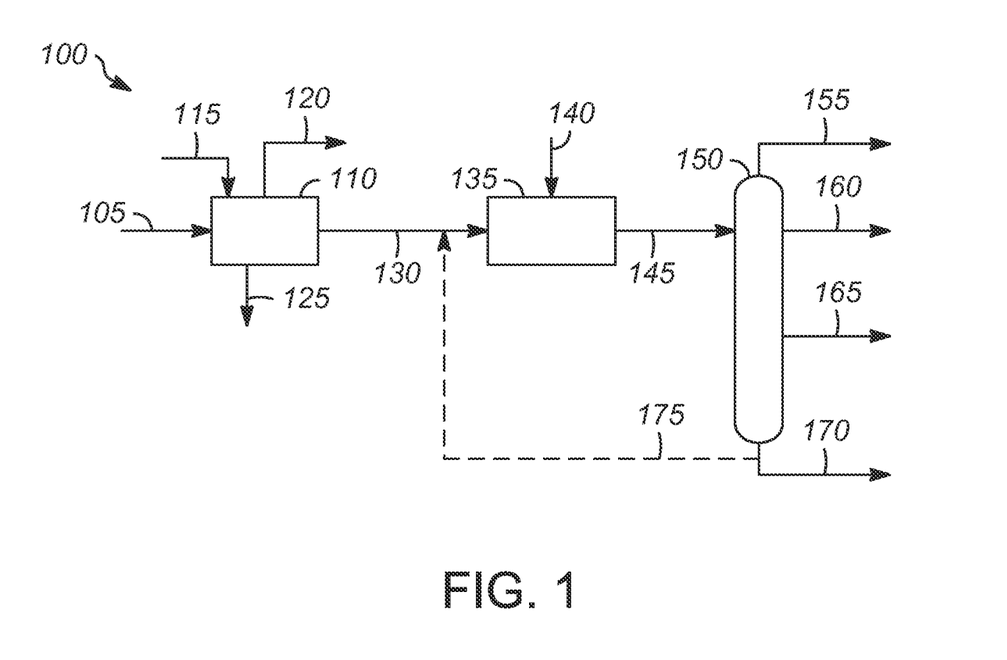
FIG. 1 illustrates one embodiment of a process for making diesel fuel and aviation fuel from renewable feedstocks.

FIG. 1 illustrates one example of such a process 100. The renewable feed 105 is sent to a hydrogenation and deoxygenation zone 110 where hydrogen 115 is added. The reaction mixture includes a liquid portion and a gaseous portion. The gaseous portion 120 comprises unreacted hydrogen, carbon dioxide, carbon monoxide, water vapor, propane and possibly sulfur, phosphorous, or nitrogen components. The liquid portion includes a hydrocarbon stream 130 and a liquid water stream 125.

The hydrocarbon stream 130, which contains n-paraffins, is sent to an isomerization and selective hydrocracking zone 135 where hydrogen 140 is added. Some n-paraffins are isomerized to branched paraffins, and some longer chain n-paraffins are hydrocracked to shorter chain paraffins.

The effluent 145 from the isomerization and selective hydrocracking zone 135 is sent to a fractionation zone 150 where it is separated into various streams including a light ends stream 155, a naphtha stream 160, an aviation fuel stream 165, and a diesel stream 170. A portion 175 of the diesel stream 170 can be recycled to improve the aviation fuel yield.

Typical isomerization and selective cracking conditions suitable for producing a large amount of aviation fuel boiling-range product for the flow scheme depicted in FIG. 1 include a temperature of about 165° C. to about 375° C. and a pressure of about 1724 kPa absolute (250 psia) to about 4826 kPa absolute (700 psia). In another embodiment, the isomerization conditions include a temperature of about 295° C. to about 375° C. and a pressure of about 3102 kPa absolute (450 psia) to about 3792 kPa absolute (550 psia). Other operating conditions for the isomerization zone are well known in the art.

Unfortunately, one side effect of making significant amounts of aviation fuel is that co-product naphtha and light ends are also produced in higher quantities at the expense of distillate yield. These naphtha and light ends co-products are undesirable because they have much lower value than the potential distillate products that could be otherwise produced.

Therefore, there is a need for a process of producing aviation fuel and diesel at high conversion rates from renewable feedstocks with lower quantities of naphtha and lights ends.

SUMMARY OF THE INVENTION

One aspect of the present invention is a process for producing both a diesel range product and an aviation range product from a renewable feedstock. In one embodiment, the process includes hydrogenating and deoxygenating the renewable feedstock by contacting the renewable feedstock and hydrogen with a hydrogenation and deoxygenation catalyst in a hydrogenation and deoxygenation zone at hydrogenating and deoxygenating conditions to provide a hydrogenation and deoxygenation zone effluent comprising paraffins, hydrogen, water, and carbon oxides. At least the paraffins are separated from the hydrogenation and deoxygenation zone effluent. The paraffins are separated into at least a diesel boiling range fraction and an aviation boiling range fraction in a first fractionation zone. The diesel boiling range fraction and the aviation boiling range fraction are alternately isomerized and selectively hydrocracked. The diesel boiling range fraction is contacted with an isomerization and selective hydrocracking catalyst in the presence of hydrogen in an isomerization and selective hydrocracking zone at first isomerization and selective hydrocracking conditions for the diesel boiling range fraction and generating a first effluent comprising at least first normal and branched paraffins in the diesel boiling point range, first normal and branched paraffins in the aviation boiling point range, first unreacted hydrogen, first naphtha, and first LPG; the first effluent is separated into a first gaseous component and a first liquid component wherein the first liquid component comprises the first normal and branched paraffins in the diesel boiling point range, the first normal and branched paraffins in the aviation boiling point range, the first naphtha, and the first LPG; and the first liquid component is separated into at least a diesel range product comprising the first normal and branched paraffins in the diesel boiling point range in a second fractionation zone. The aviation boiling range fraction is contacted with the isomerization and selective hydrocracking catalyst in the presence of hydrogen in the isomerization and selective hydrocracking zone at second isomerization and selective hydrocracking conditions for the aviation boiling range fraction and generating a second effluent comprising at least second normal and branched paraffins in the aviation boiling point range, second hydrogen, second naphtha, and second LPG; the second effluent is separated into a second gaseous component and a second liquid component wherein the second liquid component comprises the second normal and branched paraffins in the aviation boiling point range, the second naphtha, and the second LPG; and the second liquid component is separated into at least an aviation range product comprising the second normal and branched paraffins in the aviation boiling point range in the second fractionation zone.

DETAILED DESCRIPTION OF THE INVENTION

The present process meets the need for producing aviation fuel and diesel from renewable feedstocks at high conversion rates with reduced production of naphtha and light ends.

This process involves introducing the renewable feedstock into a hydrogenation and deoxygenation zone. The primary hydrocarbon effluent from the hydrogenation and deoxygenation zone is separated into an aviation boiling range fraction and a diesel boiling range fraction. The aviation boiling range fraction and the diesel boiling range fraction are alternately sent to an isomerization and selective hydrocracking zone. This allows for lower severity operating conditions in the isomerization and selective hydrocracking zone when processing oils that naturally contain medium and long carbon chains ($C_8$-$C_{18}$), such as coconut or palm kernel oil. The lower severity operation results in isomerization with decreased cracking, such that the aviation fuel yield is increased and the light ends and naphtha co-product yields are decreased relative to the conventional design shown in FIG. 1.

In the conventional process, after the intermediate water and light gas separation, the deoxygenated oil flows directly from the hydrogenation and deoxygenation zone to the isomerization and selective hydrocracking zone. This approach works satisfactorily when processing feed oils that have narrow fatty acid carbon number distribution, such as tallow and soybean oil, which are rich in $C_{16}$ and $C_{18}$ fatty acids.

However, other oils, such as coconut and palm kernel oil, have fatty acids with a greater variety of carbon numbers, typically $C_8$, $C_{10}$, $C_{12}$, $C_{14}$, $C_{16}$, and $C_{18}$. When deoxygenated, these oils yield n-paraffins between n-$C_7$ and n-$C_{18}$. Since the carbon chain length is so varied, it would better to isolate the fraction that is ideal for making diesel, e.g., n-$C_{16}$ to n-$C_{18}$, and the fraction that is ideal for making aviation fuel, e.g., n-$C_7$ to n-$C_{15}$, first and then process these fractions through the isomerization and selective hydrocracking zone separately. Separate processing allows the isomerization and selective hydrocracking zone conditions to be tailored to maximize the yield of aviation fuel while processing the n-$C_7$ to n-$C_{15}$ fraction and to maximize the yield of diesel while processing the n-$C_{16}$ to n-$C_{18}$ fraction. This also minimizes the yield of naphtha and light ends.

The conventional process flow scheme shown in FIG. 1 is modified to carry out this process. The modified design involves the addition of an n-paraffin splitter column after the hydrogenation and deoxygenation zone where the hydrocarbon effluent is separated into an aviation boiling range fraction and a diesel boiling range fraction. This is followed by intermediate storage tanks for the aviation boiling range fraction and the diesel boiling range fraction. The feed to the isomerization and selective hydrocracking zone is supplied from either the intermediate aviation storage tank or from the intermediate diesel storage tank depending on which product is desired at the time, or which tank needs to be processed due to storage constraints.

The conditions in the isomerization and hydrocracking zone are actively adjusted to maximize the desired products (aviation or diesel) depending on the feed source to the isomerization and selective hydrocracking zone. The composition of the effluent from the isomerization and selective hydrocracking zone changes when the feed source is switched from one intermediate tank to the other, Consequently, when the aviation boiling range fraction is being processed, existing diesel products are recirculated back the second fractionation zone to ensure there is always sufficient inventory in the column.

Figure 2:
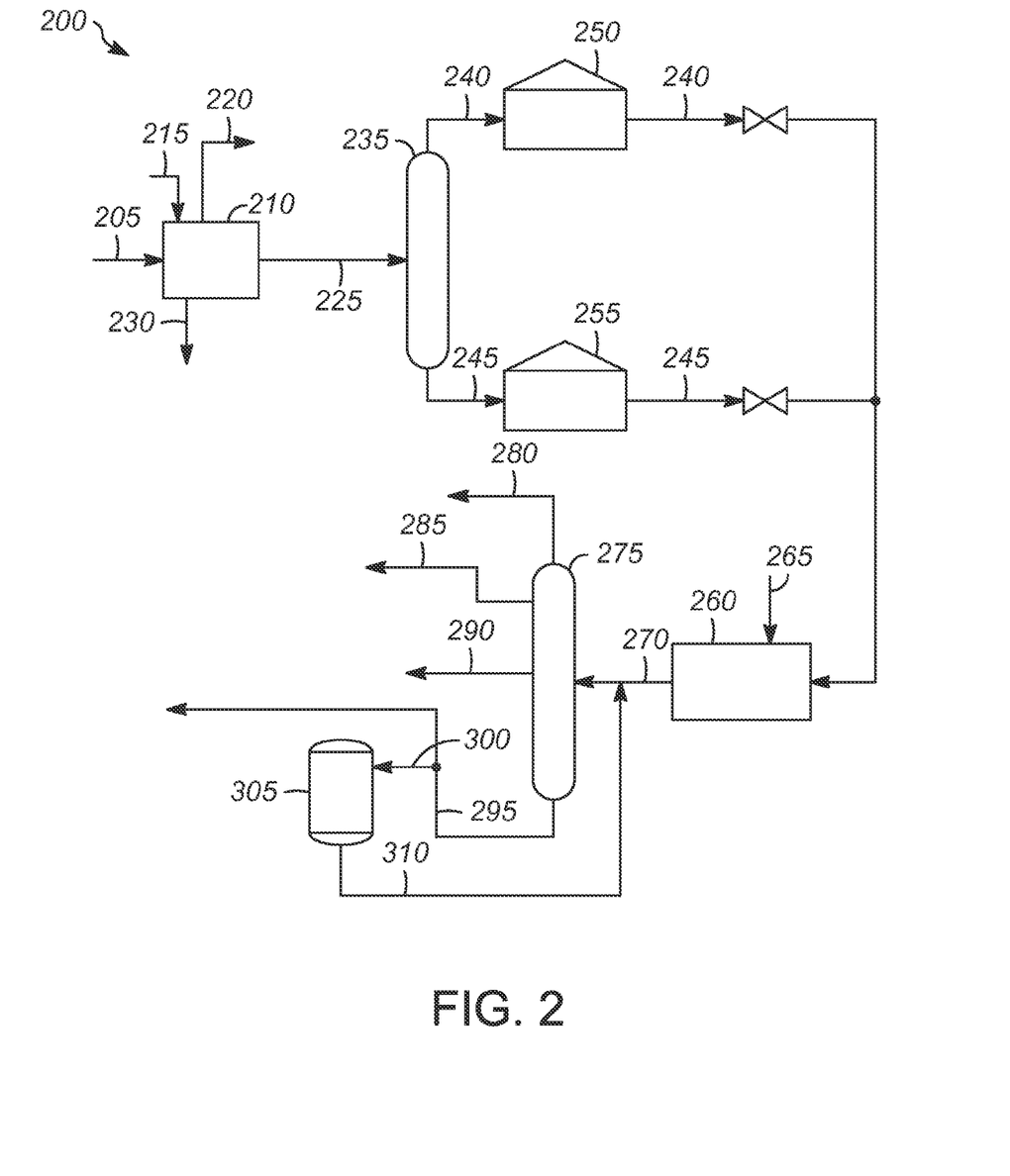
FIG. 2 illustrates one embodiment of a process for producing diesel fuel and aviation fuel from renewable feedstocks according to the present invention.

FIG. 2 illustrates one embodiment of the modified process 200. The renewable feedstock 205 is fed to the hydrogenation and deoxygenation zone 210, along with hydrogen 215.

The term renewable feedstock is meant to include feedstocks other than those obtained from petroleum crude oil. The renewable feedstocks that can be used in the present invention include any of those which comprise glycerides and free fatty acids (FFA). Examples of these feedstocks include, but are not limited to, canola oil, corn oil, soy oils, rapeseed oil, soybean oil, colza oil, tall oil, sunflower oil, hempseed oil, olive oil, linseed oil, coconut oil, castor oil, peanut oil, palm oil, palm kernel oil, babassu oil, mustard oil, cottonseed oil, inedible tallow, yellow and brown greases, lard, train oil, fats in milk, fish oil, algal oil, sewage sludge, crambe oil, palm fatty acid distillate, and the like. The glycerides and FFAs of the typical vegetable or animal fat contain aliphatic hydrocarbon chains in their structure which have about 8 to about 24 carbon atoms. Microbial oils which can be tailor made to a specified length or range of lengths can also be used (see e.g., U.S. Pat. No. 8,580,540). Modified vegetable oils which will produce a variety of n-paraffins after deoxygenation could also be used (see e.g., U.S. Pat. No. 8,916,739). Other classes of compounds include fatty acid methyl esters, and fatty acid ethyl esters. Most of the glycerides will be tri-glycerides, but monoglycerides and di-glycerides may be present and processed as well. Mixtures or co-feeds of renewable feedstocks and petroleum derived hydrocarbons may also be used as the feedstock. Other feedstock components which may be used, especially as a co-feed component in combination with the above listed feedstocks include spent motor oils and industrial lubricants, used paraffin waxes, liquids derived from the gasification of coal, biomass, natural gas followed by a downstream liquefaction step such as Fischer-Tropsch technology, liquids derived from depolymerization, thermal or chemical, of waste plastics such as polypropylene, high density polyethylene, and low density polyethylene; and other synthetic oils generated as byproducts from petrochemical and chemical processes. Mixtures of the above feedstocks may also be used as co-feed components. One advantage of using a co-feed component is the transformation of what has been considered to be a waste product from a petroleum based or other process into a valuable co-feed component to the current process.

Renewable feedstocks including renewable feedstocks that can be used in the present invention may contain a variety of impurities. For example, tall oil is a byproduct of the wood processing industry, and tall oil contains esters and rosin acids in addition to FFAs. Rosin acids are cyclic carboxylic acids. The bio-renewable feedstocks may also contain contaminants such as alkali metals, e.g. sodium and potassium, phosphorous, as well as solids, water and detergents. An optional first step (not shown) is to remove as much of these contaminants as possible. One possible pretreatment step involves contacting the renewable feedstock with an ion-exchange resin in a pretreatment zone at pretreatment conditions. The ion-exchange resin is an acidic ion exchange resin such as Amberlyst™-15, and it can be used as a bed in a reactor through which the feedstock flows, either upflow or downflow.

Another possible step for removing contaminants is a mild acid wash. This is carried out by contacting the feedstock with an acid, such as sulfuric, nitric, phosphoric, or hydrochloric, in a reactor. The acid and feedstock can be contacted either in a batch or continuous process. Contacting is done with a dilute acid solution usually at ambient temperature and atmospheric pressure. If the contacting is done in a continuous manner, it is usually done in a counter current manner. Yet another possible way of removing metal contaminants from the feedstock is through the use of guard beds which are well known in the art. These can include alumina guard beds either with or without demetallation catalysts such as nickel or cobalt. Filtration and solvent extraction techniques are other choices which may be employed. Hydroprocessing such as that described in U.S. Publication. No. 2009/0000985 is another pretreatment technique which may be employed.

The feedstock 205 is flowed to a hydrogenation and deoxygenation zone 210 comprising one or more catalyst beds in one or more reactors. The term feedstock is meant to include feedstocks that have not been treated to remove contaminants as well as those feedstocks purified in a pretreatment zone. In the hydrogenation and deoxygenation zone 210, the feedstock 205 is contacted with a hydrogenation or hydrotreating catalyst in the presence of hydrogen 215 at hydrogenation conditions to hydrogenate the olefinic or unsaturated portions of the n-paraffinic chains. Hydrogenation or hydrotreating catalysts are any of those well known in the art, such as nickel or nickel/molybdenum dispersed on a high surface area support. Other hydrogenation catalysts include one or more noble metal catalytic elements dispersed on a high surface area support. Non-limiting examples of noble metals include Pt and/or Pd dispersed on gamma-alumina. Hydrogenation conditions include a temperature of about 200° C. to about 350° C. and a pressure of about 1379 kPa absolute (200 psia) to about 5516 kPa absolute (800 psia). Other operating conditions for the hydrogenation zone are well known in the art.

The hydrogenation and hydrotreating catalysts enumerated above are also capable of catalyzing decarboxylation, decarbonylation, and/or hydrodeoxygenation of the feedstock to remove oxygen. Decarboxylation, decarbonylation, and hydrodeoxygenation are herein collectively referred to as deoxygenation reactions. Deoxygenation conditions include a relatively low pressure of about 3447 kPa (500 psia) to about 6895 kPa (1000 psia), a temperature of about 260° C. to about 345° C. and a liquid hourly space velocity of about 1 to about 4 hr$^{-1}$. Since hydrogenation is an exothermic reaction, as the feedstock flows through the catalyst bed the temperature increases and decarboxylation and hydrodeoxygenation will begin to occur. Thus, it is envisioned and is within the scope of this invention that all three reactions occur simultaneously in one reactor or in one bed. Alternatively, the conditions can be controlled such that hydrogenation primarily occurs in one bed and decarboxylation and/or hydrodeoxygenation occurs in a second bed. If only one bed is used, then hydrogenation may occur primarily at the front of the bed, while decarboxylation, decarbonylation and hydrodeoxygenation may occur mainly in the middle and bottom of the bed. Finally, desired hydrogenation can be carried out in one reactor, while decarboxylation, decarbonylation, and/or hydrodeoxygenation can be carried out in a separate reactor.

Hydrogen 215 is a reactant in the reactions above, and to be effective, a sufficient quantity of hydrogen must be in solution to most effectively take part in the catalytic reaction. In some embodiments, saturated hydrogenation/deoxygenation reactor effluent is recycled to the reactor to improve hydrogen solubility in the reactor charge stream, as hydrogen is more soluble in a mixture of reactor effluent liquid and fresh feed (such recycle is not shown in FIG. 2 for simplicity).

In general, the hydrogenation and deoxygenation conditions include a temperature of about 200° C. to about 400° C. and a pressure of about 1379 kPa absolute (200 psia) to about 13,790 kPa absolute (2000 psia).

In some embodiments, the operating pressure may be in the range of about 2413 kPa absolute (350 psia) to about 4481 kPa absolute (650 psia), and in some embodiments, the operating pressure may be in the range of about 2758 kPa absolute (400 psia) to about 4137 kPa absolute (600 psia). Lower operating pressures provide an advantage in increasing the decarboxylation reaction while reducing the hydrodeoxygenation reaction. The result is a reduction in the amount of hydrogen required to remove oxygen from the feedstock component and produce a finished product. Hydrogen can be a costly component of the feed, and reduction of the hydrogen requirements is beneficial from an economic standpoint.

In some embodiments, hydrocarbon recycle (not shown) can be used to control the temperature in the reaction zones since the reactions are exothermic reactions. In one embodiment of the invention, the volume ratio of hydrocarbon recycle to feedstock is from about 1.5:1 to about 8:1, or about 1.5:1 to about 7:1, or about 1.5:1 to about 6:1, or about 1.5:1 to about 5:1, or about 1.5:1 to about 4:1, or about 1.5:1 to about 3.5:1, or about 1.5:1 to about 3:1. The specific ranges of vol/vol ratios of recycle to feed is determined based on achieving suitable temperatures in the deoxygenation reaction zone.

The reaction product from the deoxygenation reactions in the hydrogenation and deoxygenation zone 210 will comprise a liquid portion and a gaseous portion. The gaseous portion 220 comprises hydrogen, carbon dioxide, carbon monoxide, water vapor, propane, and perhaps sulfur components such as hydrogen sulfide, nitrogen components such as ammonia, or phosphorous component such as phosphine. The separated gaseous portion comprises mostly hydrogen and the carbon oxides from the decarboxylation and decarbonylation reactions. The carbon dioxide can be removed from the hydrogen by means well known in the art, reaction with a hot carbonate solution, pressure swing absorption, etc. Also, absorption with an amine in processes such as described in US Publication Nos. 2009/0082603 and 2009/0077868 which are hereby incorporated by reference may be employed. If desired, essentially pure carbon dioxide can be recovered by regenerating the spent absorption media. The hydrogen remaining after the removal of the carbon dioxide may be recycled to either of the reaction zones. Water may also be removed from the hydrogenation and deoxygenation zone effluent.

The liquid portion 225, after water 230 is removed, comprises a hydrocarbon fraction which is essentially all n-paraffins. Different feedstocks will result in different distributions of paraffins. Although this hydrocarbon fraction may be useful as a diesel fuel or possibly an aviation fuel, because it comprises essentially all n-paraffins, it will have poor cold flow and freeze point properties. Also, depending upon the feedstock, the amount of hydrocarbons suitable for aviation fuel may be small.

In order to improve the production of diesel and aviation fuel from different feedstocks, the liquid portion 225 is separated in a first fractionation zone 235 into an aviation boiling range fraction 240 and a diesel boiling range fraction 245. The aviation boiling range fraction typically includes paraffins having in the range of 8 to 15 carbon atoms, and the diesel boiling range fraction typically has 16 or more carbon atoms. One of skill in the art will understand that there could be small amounts of paraffins having more than 15 carbon numbers in the aviation boiling range fraction, and small amounts of paraffins having less than 16 carbons in the resultant diesel boiling range fraction. Aviation fuel typically has a boiling range of about 135° C. to about 250° C. or 260° C., but may comprise components with boiling points as high as 300° C., or perhaps even higher, as specified in jet fuel specifications, such as ASTM D7566. The diesel boiling range is typically about 130° C. to about 371° C., which overlaps with the aviation boiling range, but in the context of this invention, the front end of the "diesel" would be cut via fractionation and taken as the jet product. Consequently, the resultant diesel would be heavier than full-boiling-range diesel, with an initial boiling point leaving off wherever the aviation fuel was cut out, generally between about 250° C. and about 300° C. The end point of diesel derived from most renewable oils typically would be less than 371° C., depending on the maximum number of carbon atoms found in the renewable feed oil's fatty acids. The small amounts of paraffins having more than 15 carbon atoms in the aviation fuel and less than 16 carbon atoms in the diesel fuel would be determined and controlled according to the product specifications for the freeze point limit for the aviation fuel and the flash point limit for the diesel.

Suitable operating conditions of the first fractionation zone 235 include those suitable for achieving an approximate cut point temperature of from about 270° C. to about 300° C., preferably from about 270° C. to 287° C. The cut point may be defined as the average of the $T_5$ of the heavier (diesel boiling range) hydrocarbon and the $T_{95}$ of the lighter (aviation boiling range) hydrocarbon according to the analysis of the lighter and heavier products using ASTM D2887 or ASTM D86, for example. Other methods of calculating cut point could also be used, as would be understood by those of skill in the art. The first fractionation zone 235 can include one or more fractionation columns, as needed. In other embodiments, different cut point temperatures could be targeted, depending on the desired yield and/or properties of jet and diesel products. For example, the cut point might be reduced significantly below 270° C. if additional diesel product was desired or if aviation fuel with a very low freeze point was desired. Other adjustments in the cut point could also be made, as would be understood by those of skill in the art. The conditions of the first fractionation zone may be adjusted to control the relative amounts of hydrocarbon contained in the aviation boiling range fraction 240 and the diesel boiling range fraction 245.

The aviation boiling range fraction 240 is sent to an intermediate aviation storage tank 250, and the diesel boiling range fraction 245 is sent to an intermediate diesel storage tank 255.

The isomerization and selective hydrocracking zone 260 can be alternately fed the aviation boiling range fraction 240 from the aviation storage tank 250 or the diesel boiling range fraction 245 from the diesel storage tank 255. The aviation boiling range fraction 240 or the diesel boiling range fraction 245 is contacted with an isomerization and selective hydrocracking catalyst in the presence of hydrogen 265 at isomerization and selective hydrocracking conditions to isomerize at least a portion of the normal paraffins to branched paraffins. Due to the presence of hydrogen, the reactions may be called hydroisomerization and hydrocracking.

The isomerization and selective hydrocracking of the paraffinic product can be accomplished in any manner known in the art or by using any suitable catalyst known in the art. One or more beds of catalyst may be used. It is preferred that the isomerization be operated in a co-current mode of operation. Fixed bed, trickle bed down flow or fixed bed liquid filled up-flow modes are suitable, for example.

The same catalyst is used in the isomerization and selective hydrocracking zone 260 for processing both the aviation boiling range fraction and the diesel boiling range fraction. The catalyst is selected so that the both isomerization and selective hydrocracking of the paraffins will occur. The selective hydrocracking creates additional hydrocarbons in the aviation range.

Suitable catalysts comprise a metal of Group VIII (IUPAC 8-10) of the Periodic Table and a support material. Suitable Group VIII metals include platinum and palladium, each of which may be used alone or in combination. The support material may be amorphous or crystalline. Suitable support materials include aluminas, amorphous alumina, amorphous silica-aluminas, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MgAPSO-11, MgAPSO-31, MgAPSO-41, MgAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. Nos. 4,943,424; 5,087,347; 5,158,665; and 5,208,005. MgAPSO is a MeAPSO, which is an acronym for a metal aluminum-silicophosphate molecular sieve, where the metal Me is magnesium (Mg). Suitable MgAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means an MgAPSO having structure type 31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. Nos. 4,795,623 and 4,924,027. Further catalysts and conditions for skeletal isomerization are disclosed in U.S. Pat. Nos. 5,510,306, 5,082,956, and 5,741,759.

The isomerization and selective hydrocracking catalyst may also comprise a modifier selected from the group consisting of lanthanum, cerium, praseodymium, neodymium, samarium, gadolinium, terbium, and mixtures thereof, as described in U.S. Pat. Nos. 5,716,897 and 5,851,949. Other suitable support materials include ZSM-22, ZSM-23, and ZSM-35, which are described for use in dewaxing in U.S. Pat. No. 5,246,566 and in the article entitled "New molecular sieve process for lube dewaxing by wax isomerization," written by S. J. Miller, in Microporous Materials 2 (1994) 439-449. The teachings of U.S. Pat. Nos.

4,310,440; 4,440,871; 4,793,984; 4,758,419; 4,943,424; 5,087,347; 5,158,665; 5,208,005; 5,246,566; 5,716,897; and U.S. Pat. No. 5,851,949 are hereby incorporated by reference.

U.S. Pat. Nos. 5,444,032 and 5,608,968 teach a suitable bifunctional catalyst which is constituted by an amorphous silica-alumina gel and one or more metals belonging to Group VIIIA, and is effective in the hydroisomerization of long-chain normal paraffins containing more than 15 carbon atoms. U.S. Pat. Nos. 5,981,419 and 5,908,134 teach a suitable bifunctional catalyst which comprises: (a) a porous crystalline material isostructural with beta-zeolite selected from boro-silicate (BOR—B) and boro-alumino-silicate (Al—BOR—B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. Article V. Calemma et al., App. Catal. A: Gen., 190 (2000), 207 teaches yet another suitable catalyst.

The aviation boiling range fraction 240 or the diesel boiling range fraction 245 is contacted with the isomerization and selective hydrocracking catalyst under isomerization and selective hydrocracking conditions to at least partially isomerize the n-paraffins to branched-paraffins.

The operating conditions in the isomerization and selective hydrocracking zone 260 are selected to optimize the product based on which fraction is being used.

When processing the aviation fuel fraction, the operating conditions in the isomerization and selective hydrocracking zone 260 are less severe than conditions that would be required under conventional processing to make aviation fuel, such as that represented by process 100 shown in FIG. 1, resulting in isomerization with less cracking of the longer paraffins. This increases the yield of aviation fuel while producing less lights ends and naphtha than with previous processes.

When processing the diesel fraction, since no cracking is needed, milder conditions can also be used.

Typical isomerization and selective cracking conditions include a temperature of about 150° C. to about 360° C. and a pressure of about 1724 kPa absolute (250 psia) to about 4825 kPa absolute (700 psia). In another embodiment, the isomerization conditions include a temperature of about 280° C. to about 360° C. and a pressure of about 3102 kPa absolute (450 psia) to about 3792 kPa absolute (550 psia). Other operating conditions for the isomerization zone are well known in the art.

Isomerization and selective hydrocracking can be carried out in a separate bed of the same reactor, or the isomerization and selective hydrocracking can be carried out in a separate reactor.

The effluent 270 of the isomerization and selective hydrocracking zone 260, is a branched-paraffin-enriched stream. By the term "enriched" it is meant that the effluent 270 has a greater concentration of branched paraffins than the aviation boiling range fraction 240 or diesel boiling range fraction 245 entering the isomerization and selective hydrocracking zone 260. It preferably comprises greater than 50 mass-% branched paraffins. It is envisioned that the isomerization zone effluent may contain 60, 70, 80, or 90 mass-% branched paraffins.

The effluent 270 of the isomerization and selective hydrocracking zone 260 is processed through one or more separation steps to obtain a purified hydrocarbon stream useful as a diesel fuel or a diesel fuel blending component and a purified hydrocarbon stream useful as an aviation fuel or aviation fuel blending component. Because the effluent 270 comprises both a liquid and a gaseous component, the liquid and gaseous components are separated using a separator such as a cold separator (not shown).

When the diesel range fraction is processed in the isomerization and selective hydrocracking zone 260, the liquid component includes normal and branched paraffins in the diesel boiling point range, normal and branched paraffins in the aviation boiling point range, unreacted hydrogen, naphtha, and $C_3$ and/or $C_4$ hydrocarbons (LPG). This liquid component is separated in the second fractionation zone 275 into an LPG stream 280, a naphtha stream 285, an aviation range product 290, and a diesel range product 295. A portion 300 of the diesel range product 295 can be stored in a surge drum 305.

When the aviation range fraction is processed in the isomerization and selective hydrocracking zone 260, the liquid component includes normal and branched paraffins in the aviation boiling point range, unreacted hydrogen, naphtha, and LPG. There are very little diesel range paraffins present because of the separation in the first fractionation zone 235. In this case, the liquid component is separated in the second fractionation zone 275 into an LPG stream 280, a naphtha stream 285, and an aviation range product 290. In order to properly operate the second fractionation zone 275 in this situation, diesel range product 310 from the surge drum 305 is recirculated to the second fractionation zone 275. The milder conditions in the isomerization and selective hydrocracking zone 260 result in lower yield of LPG and naphtha.

Alternatively, the column bottom liquid inventory could be used in place of the surge drum (not shown).

Suitable operating conditions for the second fractionation zone 275 include those suitable for achieving cuts between adjacent boiling products, such as cuts between LPG and naphtha, between naphtha and aviation fuel, and between aviation fuel and diesel fuel. The approximate cut point between LPG and naphtha is between about 31° C. and 97° C. The approximate cut point temperature between naphtha and aviation fuel is from about 97° C. to about 150° C., and would largely be determined by the aviation fuel flash point specification target, as typically set forth in aviation fuel specifications, such as ASTM D7566. The approximate cut point temperature between aviation fuel and diesel fuel in the context of this invention is from about 270° C. to about 300° C. The cut point between any two adjacent-boiling cuts in the second fractionation zone 275 may be defined as the average of the $T_5$ of the heavier adjacent-boiling fraction and the $T_{95}$ of the lighter adjacent-boiling fraction according to the analysis of the lighter and heavier adjacent boiling fractions using ASTM D2887 or ASTM D86, for example. Other methods of calculating cut point could also be used, as would be understood by those of skill in the art. In other embodiments, different cut point temperatures could be targeted than those described herein, depending on the desired yield and/or properties of the LPG, naphtha, aviation fuel and diesel fuel products. For example, the cut point between aviation and diesel fuel might be reduced significantly below 270° C. if additional diesel product was desired or if aviation fuel with a very low freeze point was desired. Similarly, the cut point between naphtha and aviation fuel could be significantly higher than 150° C., if an aviation fuel product with higher-than-typical flash point (38° C.) were desired. In still another scenario, it may be desirable to maximize diesel fuel production and not collect an aviation fuel product at all, allowing all or most of the material that could potentially be collected and used as aviation fuel to instead be collected as diesel fuel. In such a situation, the adjacent boiling cuts would be naphtha and diesel fuel, and the cut point temperature would largely be determined by the flash point specification target for the diesel fuel, as specified in diesel fuel specifications, such as ASTM D975. Other adjustments in the cut points could also be made, as would be understood by those of skill in the art. The second fractionation zone 275 can include one or more fractionation columns, as needed. The conditions of the second fractionation zone 275 may be adjusted to control the relative amounts of hydrocarbon contained in the LPG, naphtha, aviation and diesel range product streams.

The LPG may be sold as valuable product, burned as fuel gas in heaters required to run the processes described in this invention, or may be used in other processes such as a feed to a hydrogen production facility. Similarly, the naphtha may be used in other processes, such as the feed to a hydrogen production facility, or as feed to a naphtha cracker for light olefins production.

Depending upon the application, various additives may be combined with the diesel or aviation fuel composition generated in order to meet required specifications for different specific fuels. Therefore, the diesel range product and the aviation range product, while possible to meet the requirement of a fuel, may be used as a component for a fuel. The product may be blended with other components to form a diesel or aviation fuel, or one or more additives may be added to the product in order to form the final diesel or aviation fuel.

For example, the aviation fuel composition generated herein complies with, is a blending component for, or may be combined with one or more additives to meet at least one of: ASTM D 1655 Specification for Aviation Turbine Fuels Defense Stan 91-91 Turbine Fuel, Aviation Kerosene Type, Jet A-1 NATO code F-35, F-34, F-37 Aviation Fuel Quality Requirements for Jointly Operated Systems (Joint Checklist) A combination of ASTM and Def Stan requirements GOST 10227 Jet Fuel Specifications (Russia) Canadian CAN/CGSB-3.22 Aviation Turbine Fuel, Wide Cut Type Canadian CAN/CGSB-3.23 Aviation Turbine Fuel, Kerosene Type MIL-DTL-83133, JP-8, MIL-DTL-5624, JP-4, JP-5 QAV-1 (Brazil) Especifcacao de Querosene de Aviacao No. 3 Jet Fuel (Chinese) according to GB6537 DCSEA 134A (France) Carbureacteur Pour Turbomachines D'Aviation, Type Kerosene Aviation Turbine Fuels of other countries, meeting the general grade requirements for Jet A, Jet A-1, Jet B, and TS-1 fuels as described in the IATA Guidance Material for Aviation Turbine Fuel Specifications. The aviation fuel is generally termed "jet fuel" herein and the term "jet fuel" or aviation fuel is meant to encompass aviation fuel meeting the specifications above as well as to encompass aviation fuel used as a blending component of an aviation fuel meeting the specifications above. Additives may be added to the jet fuel in order to meet particular specifications. One particular type of jet fuel is JP-8, defined by Military Specification MIL-DTL-83133, which is a military grade type of highly refined kerosene based jet propellant specified by the United States Government. The fuel produced from glycerides and FAAs is very similar to isoparaffinic kerosene or iPK, also known as a synthetic jet fuel.

The specifications for different types of fuels are often expressed through acceptable ranges of chemical and physical requirements of the fuel. As stated above, aviation turbine fuels, a kerosene type fuel including JP-8, are specified by MIL-DTL-83133, JP-4, a blend of gasoline, kerosene and light distillates, is specified by MIL-DTL-5624 and JP-5 a kerosene type fuel with low volatility and high flash point is also specified by MIL-DTL-5624, with the written specification of each being periodically revised. Often a distillation range from 10 percent recovered to a final boiling point is used as a key parameter defining different types of fuels. The distillations ranges are typically measured by ASTM Test Method D 86 or D2887. Therefore, blending of different components in order to meet the specification is quite common. While the product of the present invention may meet fuel specifications, it is expected that some blending of the product with other blending components may be required to meet the desired set of fuel specifications. In other words, the aviation product of this invention is a composition which may be used with other components to form a fuel meeting at least one of the specifications for aviation fuel such as JP-8. The desired products are highly paraffinic distillate fuel components having a paraffin content of at least 75% by volume. The aviation fuel produced by the present process can be used as a blending component in an aviation fuel meeting the specifications of ASTM D7566 or other aviation fuel specifications that include renewable components.

In some embodiments, all or a portion of the diesel-range product 295 can be recycled back to the isomerization and selective hydrocracking zone 260 to be further cracked into jet-range product (not shown in FIG. 2).

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for producing both a diesel range product and an aviation range product from a renewable feedstock comprising:

hydrogenating and deoxygenating the renewable feedstock by contacting the renewable feedstock and hydrogen with a hydrogenation and deoxygenation catalyst in a hydrogenation and deoxygenation zone at hydrogenating and deoxygenating conditions to provide a hydrogenation and deoxygenation zone effluent comprising paraffins, hydrogen, water, and carbon oxides;

separating at least the paraffins from the hydrogenation and deoxygenation zone effluent;

separating the paraffins into at least a diesel boiling range fraction and an aviation boiling range fraction in a first fractionation zone;

isomerizing and selectively hydrocracking the diesel boiling range fraction and the aviation boiling range fraction by alternately:

contacting the diesel boiling range fraction with an isomerization and selective hydrocracking catalyst in the presence of hydrogen in an isomerization and selective hydrocracking zone at first isomerization and selective hydrocracking conditions for the diesel boiling range fraction and generating a first effluent comprising at least first normal and branched paraffins in the diesel boiling point range, first normal and branched paraffins in the aviation boiling point range, first unreacted hydrogen, first naphtha, and first LPG;

separating the first effluent into a first gaseous component and a first liquid component wherein the first liquid component comprises the first normal and branched paraffins in the diesel boiling point range, the first normal and branched paraffins in the aviation boiling point range, the first naphtha, and the first LPG; and separating the first liquid component into at least a diesel range product comprising the first normal and branched paraffins in the diesel boiling point range in a second fractionation zone;

or:

contacting the aviation boiling range fraction with the isomerization and selective hydrocracking catalyst in the presence of hydrogen in the isomerization and selective hydrocracking zone at second isomerization and selective hydrocracking conditions for the aviation boiling range fraction and generating a second effluent comprising at least second normal and branched paraffins in the aviation boiling point range, second hydrogen, second naphtha, and second LPG;

separating the second effluent into a second gaseous component and a second liquid component wherein the second liquid component comprises the second normal and branched paraffins in the aviation boiling point range, the second naphtha, and the second LPG; and separating the second liquid component into at least an aviation range product comprising the second normal and branched paraffins in the aviation boiling point range in the second fractionation zone.

2. The method of claim 1 wherein separating the second liquid component into at least the aviation range product in the second fractionation zone comprises separating the second liquid component into at least the aviation range product; further comprising:
recycling at least a portion of the first diesel range product to the second fractionation zone.

3. The method of claim 1 wherein:
separating the first liquid component into at least the first diesel range product in the second fractionation zone comprises separating the first liquid component into at least the first diesel range product, a first aviation range product comprising the first normal and branched paraffins in the aviation boiling point range, a first naphtha product comprising the first naphtha, and a first LPG product comprising the first LPG;

or separating the second liquid component into at least the second aviation range product in the second fractionation zone comprises separating the second liquid component into at least the second aviation range product, a second naphtha product comprising the second naphtha, and a second LPG product comprising the second LPG;

or both.

4. The method of claim 1 further comprising:
storing the diesel boiling range fraction in an intermediate diesel storage tank and storing the aviation boiling range fraction in an intermediate aviation storage tank; and alternately feeding the diesel boiling range fraction from the intermediate diesel storage tank to the isomerization and selective hydrocracking zone and feeding the aviation boiling range fraction from the intermediate aviation storage tank to the isomerization and selective hydrocracking zone.

5. The method of claim 1 wherein at least one of the first or second isomerization and selective hydrocracking conditions include a temperature of about 150° C. to about 360° C. and a pressure of about 1724 kPa absolute (250 psia) to about 4825 kPa absolute (700 psia).

6. The method of claim 1 wherein hydrogenating and deoxygenating conditions include a temperature of about 200° C. to about 400° C. and a pressure of about 1379 kPa absolute (200 psia) to about 6895 kPa absolute (1000 psia).

7. The method of claim 1 wherein the diesel boiling range fraction comprises paraffins having 16 or more carbon atoms and wherein the aviation boiling range fraction comprises paraffins having 8 to 15 carbon atoms.

8. The method of claim 1 wherein the renewable feedstock comprises a vegetable oil or an animal oil.

9. The method of claim 1 wherein the renewable feedstock comprises at least one component selected from the group consisting of canola oil, corn oil, soy oil, rapeseed oil, soybean oil, colza oil, tall oil, sunflower oil, hempseed oil, olive oil, linseed oil, coconut oil, castor oil, peanut oil, palm oil, palm kernel oil, babassu oil, mustard oil, cottonseed oil, inedible tallow, yellow and brown greases, lard, train oil, fats in milk, fish oil, algal oil, sewage sludge, pyrolysis oil, liquids derived from the gasification of coal, liquids derived from depolymerization, synthetic oils, microbial oils, modified vegetable oils, and mixtures thereof.

10. The method of claim 1 wherein the isomerization and selective hydrocracking conditions include a temperature of about 280° C. to about 360° C. and a pressure of about 3102 kPa absolute (250 psia) to about 3792 kPa absolute (550 psia).

11. The method of claim 1 further comprising pre-treating the renewable feedstock in a pretreatment zone at pretreatment conditions to remove at least a portion of contaminants in the feedstock.

12. The method of claim 1 wherein the renewable feedstock is in a mixture or co-feed with a petroleum hydrocarbon feedstock.

13. A process for producing both a diesel range product and an aviation range product from a renewable feedstock comprising:

hydrogenating and deoxygenating the renewable feedstock by contacting the renewable feedstock and hydrogen with a hydrogenation and deoxygenation catalyst in a hydrogenation and deoxygenation zone at hydrogenating and deoxygenating conditions to provide a hydrogenation and deoxygenation zone effluent comprising paraffins, hydrogen, water, and carbon oxides;

separating at least the paraffins from the hydrogenation and deoxygenation zone effluent;

separating the paraffins into at least a diesel boiling range fraction and an aviation boiling range fraction in a first fractionation zone;

storing the diesel boiling range fraction in an intermediate diesel storage tank and storing the aviation boiling range fraction in an intermediate aviation storage tank;

isomerizing and selectively hydrocracking the diesel boiling range fraction and the aviation boiling range fraction by alternately:

contacting the diesel boiling range fraction from the intermediate diesel storage tank with an isomerization and selective hydrocracking catalyst in the presence of hydrogen in an isomerization and selective hydrocracking zone at first isomerization and selective hydrocracking conditions for the diesel boiling range fraction and generating a first effluent comprising at least first normal and branched paraffins in the diesel boiling point range, first normal and branched paraffins in the aviation boiling point range, first unreacted hydrogen, first naphtha, and first LPG;

separating the diesel range effluent into a first gaseous component and a first liquid component wherein the first liquid component comprises the first normal and branched paraffins in the diesel boiling point range, the first normal and branched paraffins in the aviation boiling point range, the first naphtha, and the first LPG; and separating the first liquid component into at least a diesel product comprising the first normal and branched paraffins in the diesel boiling point range, a first aviation product comprising the first normal and branched paraffins in the aviation boiling point range, a first naphtha product comprising the first naphtha, and a first LPG product comprising the first LPG in a second fractionation zone;

or:

contacting the aviation boiling range fraction from the intermediate aviation storage tank with the isomerization and selective hydrocracking catalyst in the presence of hydrogen in the isomerization and selective hydrocracking zone at second isomerization and selective hydrocracking conditions for the aviation boiling range fraction and generating a second effluent comprising at least second normal and branched paraffins in the aviation boiling point range, second hydrogen, second naphtha, and second LPG;

separating the aviation range effluent into a second gaseous component and a second liquid component wherein the second liquid component comprises the second normal and branched paraffins in the aviation boiling point range, the second naphtha, and the second LPG; and separating the second liquid component into at least a second aviation product comprising the second normal and branched paraffins in the aviation boiling point range, a second naphtha product comprising the second naphtha, and a second LPG product comprising the second LPG in the second fractionation zone.

14. The method of claim 13 further comprising recycling at least a portion of the first diesel range product to the second fractionation zone.

15. The method of claim 13 wherein the first isomerization and selective hydrocracking conditions include a temperature of about 150° C. to about 360° C. and a pressure of about 1724 kPa absolute (250 psia) to about 4825 kPa absolute (700 psia).

16. The method of claim 13 wherein hydrogenating and deoxygenating conditions include a temperature of about 200° C. to about 400° C. and a pressure of about 1379 kPa absolute (200 psia) to about 6895 kPa absolute (1000 psia).

17. The method of claim 13 wherein the diesel boiling range portion comprises paraffins having 16 or more carbon atoms and wherein the aviation boiling range portion comprises paraffins having 8 to 15 carbon atoms.

18. The method of claim 13 wherein the renewable feedstock comprises at least one component selected from the group consisting of canola oil, corn oil, soy oil, rapeseed oil, soybean oil, colza oil, tall oil, sunflower oil, hempseed oil, olive oil, linseed oil, coconut oil, castor oil, peanut oil, palm oil, palm kernel oil, babassu oil, mustard oil, cottonseed oil, inedible tallow, yellow and brown greases, lard, train oil, fats in milk, fish oil, algal oil, sewage sludge, pyrolysis oil, liquids derived from the gasification of coal, liquids derived from depolymerization, synthetic oils, microbial oils, modified vegetable oils, and mixtures thereof.

19. The method of claim 13 wherein the isomerization and selective hydrocracking conditions include a temperature of about 280° C. to about 360° C. and a pressure of about 3102 kPa absolute (250 psia) to about 3792 kPa absolute (550 psia).

20. The method of claim 13 further comprising pretreating the renewable feedstock in a pretreatment zone at pretreatment conditions to remove at least a portion of contaminants in the feedstock.

* * * * *